(12) United States Patent
Zschaeck et al.

(10) Patent No.: US 9,314,611 B2
(45) Date of Patent: Apr. 19, 2016

(54) STIMULATION DEVICE

(71) Applicant: cerbomed GmbH, Erlangen (DE)

(72) Inventors: Thomas Zschaeck, Nuremberg (DE);
Stefan Baer, Cadolzburg (DE); Andreas Hartlep, Holzkirchen (DE); Wolf Gerhard Frenkel, Inzigkofen-Engelswies (DE)

(73) Assignee: CERBOMED GMBH, Erlangen (DE)

( * ) Notice: Subject to any disclaimer, the term of this patent is extended or adjusted under 35 U.S.C. 154(b) by 0 days.

(21) Appl. No.: 14/525,530

(22) Filed: Oct. 28, 2014

(65) Prior Publication Data
US 2015/0119968 A1    Apr. 30, 2015

(30) Foreign Application Priority Data

Oct. 28, 2013  (DE) .................. 10 2013 017 889

(51) Int. Cl.
| | |
|---|---|
| *A61N 1/00* | (2006.01) |
| *A61N 1/04* | (2006.01) |
| *A61H 39/00* | (2006.01) |
| *A61N 1/36* | (2006.01) |

(52) U.S. Cl.
CPC .............. *A61N 1/048* (2013.01); *A61H 39/002* (2013.01); *A61N 1/0456* (2013.01); *A61N 1/0472* (2013.01); *A61N 1/36014* (2013.01); *A61N 1/36032* (2013.01); *A61H 2201/0157* (2013.01); *A61H 2205/027* (2013.01)

(58) Field of Classification Search
CPC ..... A61N 1/0472; A61N 1/02; A61N 1/0456; A61N 1/048; A61N 1/0541
See application file for complete search history.

(56) References Cited

U.S. PATENT DOCUMENTS

| | | | |
|---|---|---|---|
| 8,666,502 B2 | 3/2014 | Hartlep et al. | |
| 8,688,239 B2 | 4/2014 | Hartlep et al. | |
| 8,751,020 B2 | 6/2014 | Beck et al. | |
| 2011/0166624 A1* | 7/2011 | Dietrich et al. ................. | 607/57 |

FOREIGN PATENT DOCUMENTS

| | | |
|---|---|---|
| DE | 102010054165 B3 | 5/2012 |
| DE | 102012014714 A1 | 9/2013 |
| DE | 102012014764 A1 | 9/2013 |
| DE | 102012019834 A1 | 4/2014 |

* cited by examiner

*Primary Examiner* — Robert N Wieland
(74) *Attorney, Agent, or Firm* — Lucas & Mercanti, LLP

(57) ABSTRACT

A stimulation device for the application of a transcutaneous electric stimulation stimulus onto the surface of a section of the human ear, which includes a holding element an electrode arranged in a electrode carrier. The holding element has a linear guide. A resting part is arranged at the holding element. The holding rod has a first axis and runs from a first position, which adjoins to the linear guide, to a second position, which adjoins to the electrode carrier. The resting part defines a first plane with a resting area at the ear, on which area a second axis is arranged perpendicular. The first axis and the second axis span a middle plane. The holding rod lies at the first position in the middle plane and departs from the middle plane from the run from the first position to the second position in a first rod section until a reversal point. The holding rod moves to the middle plane from the run from the reversal point to the second position in a second rod section, so that it lies in the middle plane after arriving at the second position.

11 Claims, 3 Drawing Sheets

STIMULATION DEVICE

The present application claims priority of DE 10 2013 017 889.4, filed Oct. 28, 2013, the priority of this application is hereby claimed and this application is incorporated herein by reference.

BACKGROUND OF THE INVENTION

The invention relates to a stimulation device for the application of a transcutaneous electric stimulation stimulus onto the surface of a section of the human ear, which comprises a holding element which can be attached at or in the ear as well as at least one electrode which is arranged in a electrode carrier, wherein the holding element comprises a linear guide in which a holding rod is arranged linear movably in the direction of a longitudinal axis of the holding element, wherein the electrode carrier is arranged at an axial end of the holding rod which is remote from the linear guide, wherein a resting part is arranged or formed at the holding element which resting part is designed for resting on a section of the ear, wherein the holding rod comprises a first axis which runs in the region of the linear guide and parallel to the longitudinal axial of the holding rod, wherein the holding rod runs from a first position, which adjoins to the linear guide, to a second position, which adjoins to the electrode carrier, wherein the resting part defines a first plane with a resting area at the ear, on which area a second axis is arranged perpendicular, wherein the first axis and the second axis span a middle plane.

A stimulation device of the generic kind is known from DE 10 2012 014 764 A1 Such a stimulation device has proven itself to administer by the method of the transcutaneous electrical nerve stimulation pulse currents of different current forms, amplitudes, pulse durations and frequencies through the skin on different nerves and so to treat different diseases.

At the pre-known stimulation device the holding rod crosses over—coming from the region of the linear guide—in a leaf spring like formed region which is indeed angled against the section in the region of the linear guide but runs linear to the electrode carrier.

It has been found that at this pre-known solution it is not always ensured that the electrode carrier with the electrodes can be placed in an ergonomic beneficial manner on the skin surface and simultaneously a high wearing comfort is ensured.

SUMMARY OF THE INVENTION

Thus, it is an object of the invention, to further develop a stimulation device of the generic kind so that the mentioned drawback is eliminated. Thus, a further development should be proposed in that effect that a better stimulation is enabled by an improved placement of the electrodes on the skin surface of the ear, wherein simultaneously a high level for the wearing comfort of the stimulation device is obtained.

The solution of this object by the invention is characterized in that the holding rod lies at the first position in the or near the middle plane, that the holding rod departs from the middle plane from the run from the first position to the second position in a first rod section until a reversal point, that the holding rod moves to the middle plane from the run from the reversal point to the second position in a second rod section, so that it lies in the or near the middle plane after arriving of the second position.

The holding rod runs—in difference to the pre-known solution as discussed above—thus from the linear guide to the electrode carrier not linear but draws aside laterally. So, the electrode carrier can be guided in an improved manner and ergonomic beneficial to the location of the skin surface of the ear, especially in the region of the Cymba conchae which hat to be charged with a transcutaneous stimulation current.

By the run of the holding rod which has a S-shaped double swung form in the space the holding rod has a spring effect with a relatively flat path-(counter)force-curve respectively-pressure-curve compared with a linear run. Thereby, pressure marks at the skin of the ear are avoided at nevertheless optimized electrode contact. This property can also be promoted by a respective choice of the material so that pressure marks in the Cymba conchae can be avoided.

Thereby, the holding rod sinks preferably between the first position and the second position, measured in the direction of the second axis, by a height displacement into the direction of the first plane. The distance from the middle plane of the holding rod in the reversal point is preferably between 30% and 60% of the height displacement.

The holding rod has preferably a tangent at the first position which is directed into the direction of the first axis. Meanwhile it is preferably furthermore provided that the holding rod has a tangent at the entry in the electrode carrier at the second position which encloses an angle to the first axis which is between 50° and 80°, seen in the direction of the second axis.

The holding rod has preferably a swung run without any kink along its whole run from the first position to the second position.

The holding rod consists preferably of an elastic material, especially of plastic material, at least in the region between the first position and the second position.

The electrical power supply of the at least one electrode can take place from the holding element via a cable, which runs separately between the holding element and the electrode carrier.

The holding rod can thereby consist of two parts, namely of a first (linear) part, which runs in the linear guide, and a second part (formed S-shaped swung), which runs between the first position and the second position. The two parts of the holding rod are thereby preferably connected with another by means of a form fit connection.

It can be reached with the proposed solution in a very beneficial manner that the stimulation device with the resting area of the resting part can be placed in such a way in the ear that the resting part rest below the Tragus in the Cavum conchae, that however the electrode carrier with its electrodes is guided ergonomically beneficial and with a high wearing comfort for resting in the region of the Cymba conchae. In regard to this design reference is made explicitly to DE 10 2012 014 764 A1 of the applicant where details for this are explained.

The stimulation device can be equipped with miscellaneous elements with respect to its detailed embodiment as they are described in DE 10 2010 054 165 B3 and in the already above mentioned DE 10 2012 014 764 A1. Explicitly reference is made to those two pre-known embodiments of the applicant. This applies especially with respect to the design and the arrangement of the electrodes at the electrode carrier as well as for the design of the linear guide and the resting part.

From the above comments it is to be understood that by term "holding element" not only a linear extending element has to be understood; only in the region of the linear guide a linear design of the holding rod is given. Apart from that the holding rod runs between the linear guide and the electrode carrier in the explained S-shaped swung form.

The holding rod can for example comprise a core from elastic material, especially metal (specifically preferred spring steel), wherein this core is embedded in a cover material, especially in a bio-compatible plastic material; therefore, specifically silicon, polyamides polypropylene or polyurethane has proven itself.

Also the electrode carrier can consist at least partially from elastic material, especially from bio-compatible plastic material, specifically preferred from silicon, polyethylene, polypropylene or polyurethane.

The electrode carrier comprises, especially designed as electrode head, preferably at least one stimulation electrode and at least one reference electrode.

The electrodes are preferably metal electrodes, especially titan electrodes. They have preferably the shape of a spherical segment or of a section of an ellipsoid.

The parts of the stimulation device are preferably exchangeable—as far as skin contact is given—and consist of a soft material, wherein specifically an elastomers material it taken into account, specifically silicone or a material which comprises silicone. In the case of the electrode carrier a simple exchangeablility can be obtained in that the cable is designed insertable in the electrode carrier.

Furthermore, the following developments of the proposed concept have proven itself as very beneficial:

The two parts of the holding rod can consists of materials of different elasticity and thus with a different reset force at a deformation.

Furthermore, a concept is very beneficial wherein a set of several second parts of the holding rod is provided. Those second parts differ in its geometry and/or in the used material and thus in its spring force respectively reset force which can be specifically influenced by the design respectively by the choice of the material. A significant geometrical influence factor is especially the size of the radii of the double-swung formed holding rod. It is the benefit here that an optimized second part of the holding rod can be chosen and used from the physician or user respectively patient. So, the holding rod can be adapted to the contour of the ear and the sensibility of the patient.

The cable respectively the electrically conductive litz wires can run at least partially within the holding rod.

Also, it can be provided that a core made from bendable material (preferably made of metal) runs at least within the second part of the holding rod by which the holding rod can be bent from a first position into a second one. So, the user of the device can bend the holding rod according to an individual relief of the respective ear.

In the drawing an embodiment of the invention is depicted.

DETAILED DESCRIPTION OF THE INVENTION

Figure 1:
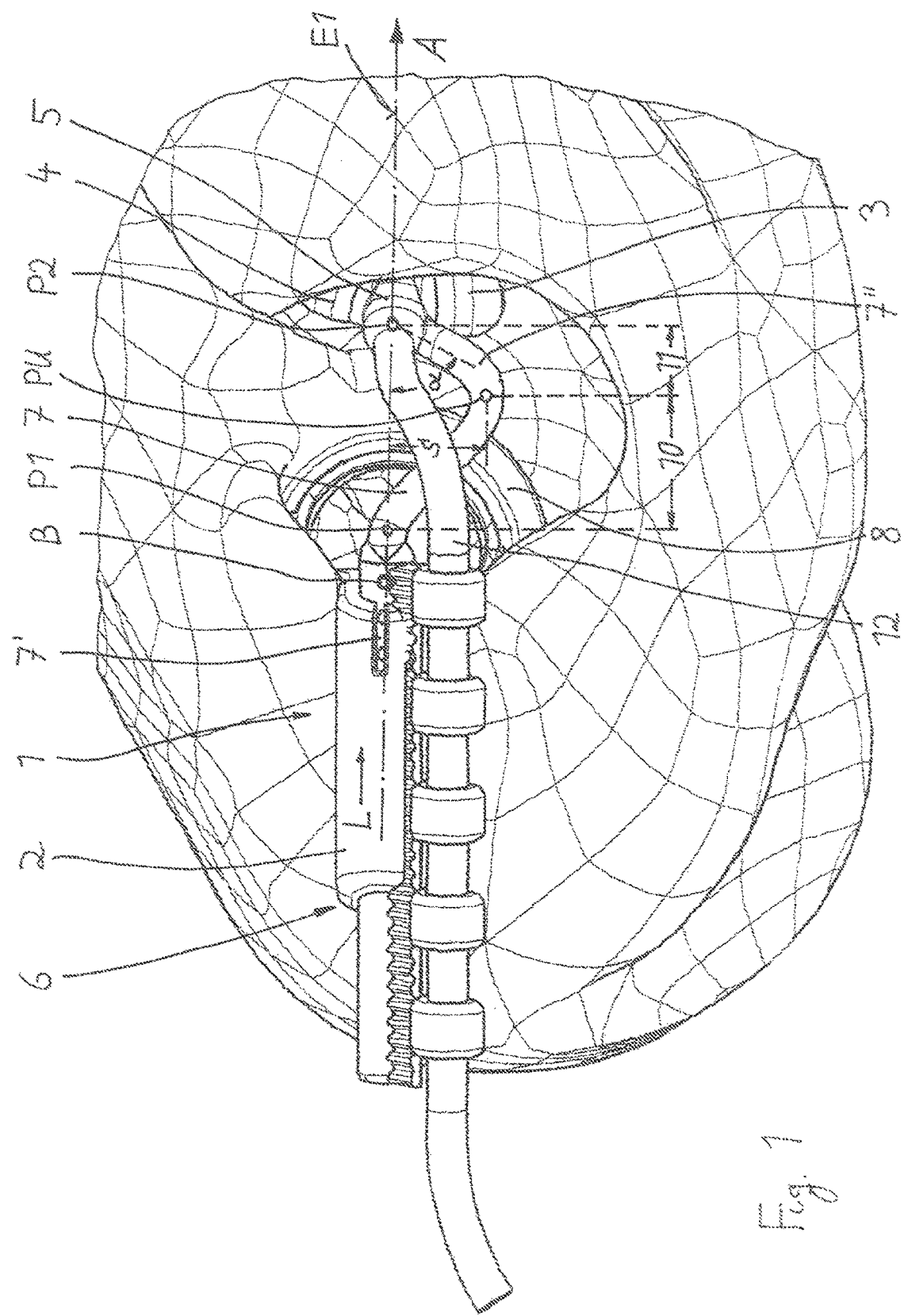
FIG. 1 shows the top plan view of a stimulation device which is inserted into an ear of a human.
Figure 2:
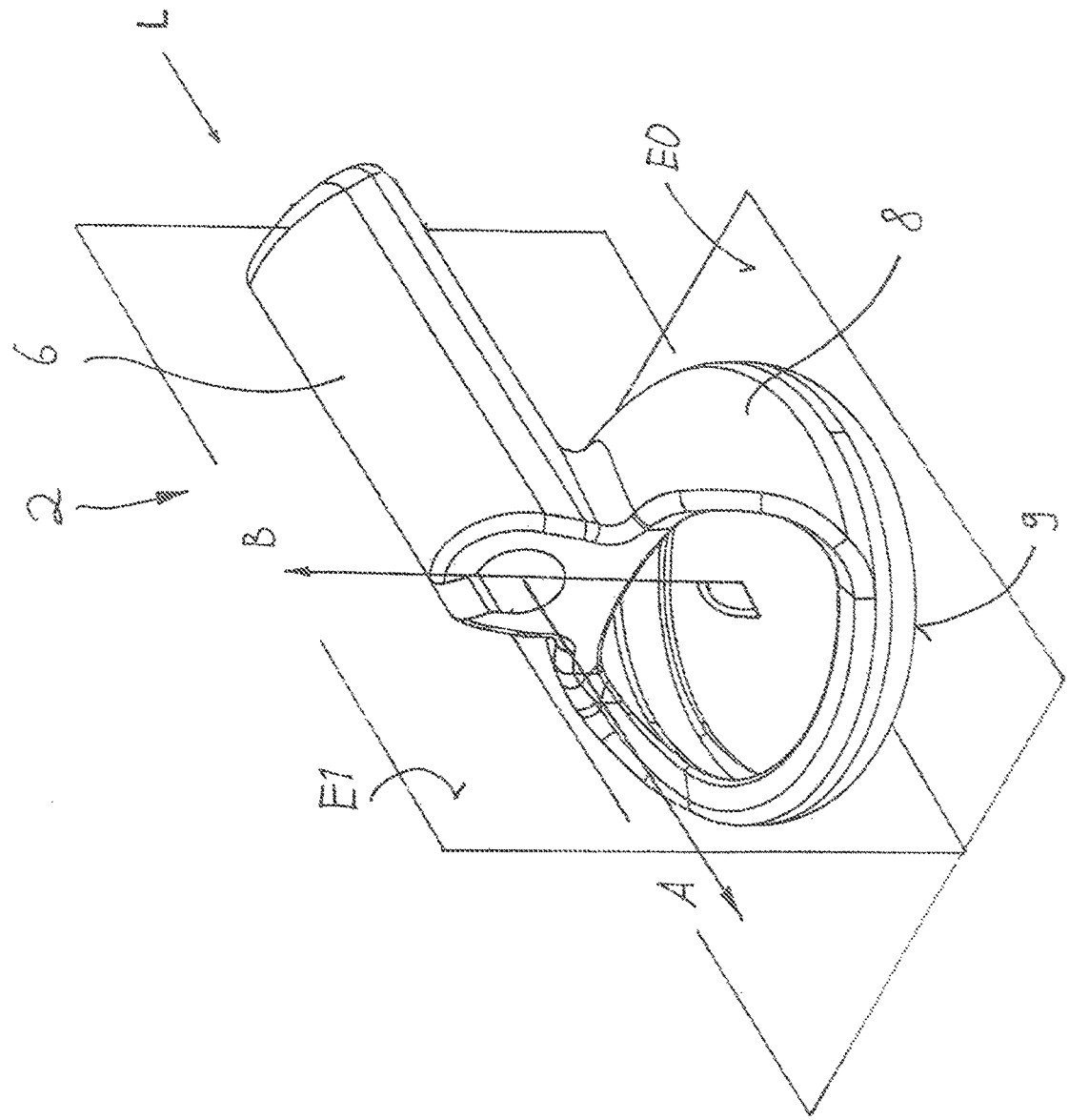
FIG. 2 shows the perspective view of the holding element of the stimulation device with a resting part which is formed with it and FIG. 3 shows the perspective view of a part of the holding element of the stimulation device.

In FIG. 1 a stimulation device 1 is shown which is inserted in a partially depicted ear of a patient. With the stimulation device a transcutaneous nerve stimulation is carried out. Central part of the stimulation device 1 is a holding element 2 which is shown in FIG. 2 as single part. The holding element 2 has a linear guide 6 in which a holding rod 7 (see FIG. 1) is arranged linear movable in the direction of a longitudinal axis L.

At one of the axial ends of the holding rod 7 an electrode carrier 5 is arranged which carries two electrodes 3, 4, namely a stimulation electrode and a reference electrode.

Furthermore, at the holding element 2 a resting part 8 is formed which has a resting area 9 (see FIG. 2) which is designed for resting in the Cavum conchae of the ear. When the stimulation device 1 lies in this manner in the ear see in this respect FIG. 1 the holding rod 7 extends in the Cymba conchae with the electrode carrier 5 which is arranged at its end, so that the two electrodes 3, 4 rest here on the skin and can stimulate transcutaneously.

With respect to details explicitly reference is made to DE 10 2010 054 165 B2 and DE 10 2012 014 764 A1 where for this detailed explanations are given.

As can be seen in the synopsis of the figures the holding rod 7 has a straight run in the region in which it runs in the linear guide 6 which is characterized by a first axis A which runs parallel to the longitudinal axis L respectively which is identical with the same. If the resting part 8 is regarded with the resting area 9 lying in the Cavum conchae it has to be stated that a first plane E0 can be defined which results by the resting area 9. A second axis B is perpendicular to this plane E0. The two axes A and B span a middle plane E1.

Figure 3:
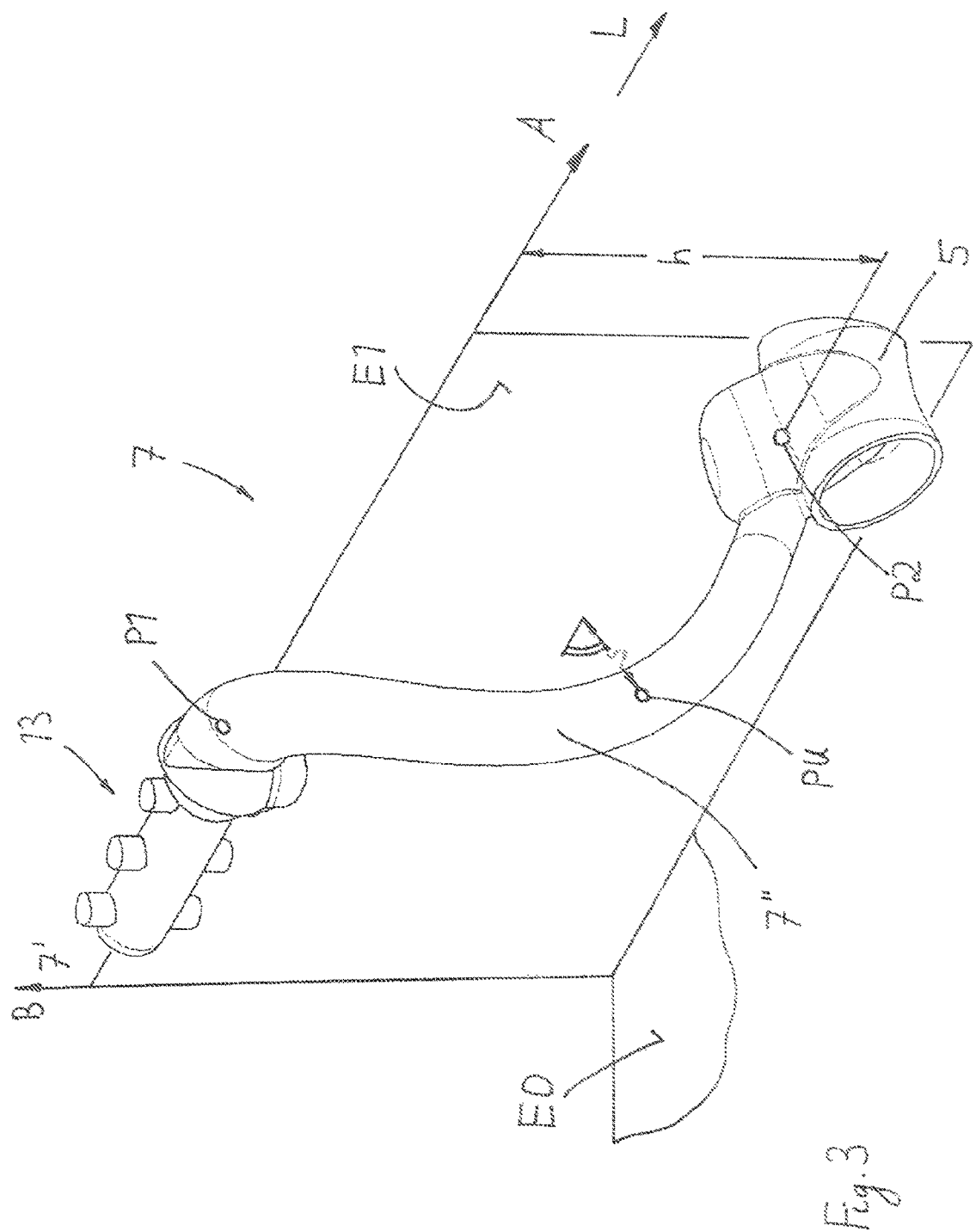

As results with regard to this definitions it is provided that the holding rod 7 runs from a first position P1 (see FIG. 1 and FIG. 3), which adjoins to the linear guide 6, to a second position P2, which adjoins to the electrode carrier 5. The holding rod 7 lies at the first position P1 in the middle plane E1 respectively it is at least positioned close to it. Then, the holding rod 7 departs from the middle plane E1 during its run from the first position P1 to the second position P2 in a first rod section 10 till a reversal point PU, i. e. the shortest distance of the holding rod 7 from the plane E1 rises permanently. However, the holding rod 7 moves back again to the middle plane E1 during its run from the reversal point PU to the second position P2 in a second rod section 11. In the second position P2 the middle plane E1 is reached again respectively the holding rod 7 lies here again at least close to the middle plane E1. The maximal distance is denoted with s which the holding rod 7 has in the reversal point PU from the middle plane E1.

As can be furthermore seen the holding rod 7 runs between the position P1 and P2 not only in the described manner swung from the middle plane E1 away and then back to the same but the electrode carrier 5 is guided also from the height of the linear guide 6 by a height displacement h downwards in the direction to the skin surface.

As also can be further seen the holding rod 7 has a tangent at the first position P1 which is directed in the first axis A. Meanwhile, it can be seen—in this respect it is referred to FIG. 1—that the holding rod 7 has a tangent at the entry in the electrode carrier 5 at the second position P2 which in the top plan view according to FIG. 1 includes an angle α to the first axis A; this angle lies in the embodiment at approximately 55°, preferably it lies between 50° and 80°.

The holding rod 7 is presently designed in two parts. A first part 7' is that region which runs in the linear guide 6. A second part 7" is however that part (depicted in FIG. 3) which comprises the swung S-shaped run and forms the connection between the first position P1 and the second position P2.

The holding rod 7 is made from those two parts 7' and 7" which are produced separately and are then connected with another by means of a form fit connection 13. For this purpose the part 7" has in the embodiment several cylindrical knobs which extend radially from the rod base body which mesh which corresponding receptions in the part 7' (not depicted); the section of the part 7', in which the part 7" engages, is therefore designed as sleeve in which the axial end of the part 7" can enter. The parts 7' and 7" can so be stuck together and hereby firmly connected.

However, at the choice of a respective material which is also sufficiently stable in its form to run without problems in the linear guide and nevertheless has the above described spring property the holding rod can also be formed and produced as a one-piece part.

The power supply of the electrodes 3, 4 takes place by means of a cable 12. Details concerning this are again explained in DE 10 2010 054 165 B3 and DE 10 2012 014 764 A1 so that insofar reference can be made to those documents.

The mechanical connection of the electrode carrier 5 including electrodes 3, 4 with the holding element 2 is thus established by the holding rod 7 and especially its part 7", while the electrical connection is established by the cable 12 which is resilient and flexible compared with the holding rod 7.

LIST OF REFERENCES

1 Stimulation device
2 Holding element
3 Electrode
4 Electrode
5 Electrode carrier
6 Linear guide
7 Holding rod
7' First part of the holding rod
7" Second part of the holding rod
8 Resting part
9 Resting area
10 First rod section
11 Second rod section
12 Cable
13 Form fit connection
L Longitudinal axis
A First axis
B Second axis
P1 First position
P2 Second position
PU Reversal point
E0 First plane
E1 Middle plane
h Height displacement
s Distance from the middle plane
α Angle

The invention claimed is:

1. A stimulation device for the application of a transcutaneous electric stimulation stimulus onto the surface of a section of the human ear, which comprises a holding element which can be attached at or in the ear as well as at least one electrode which is arranged in a electrode carrier,
wherein the holding element comprises a linear guide in which a holding rod is arranged linear movably in the direction of a longitudinal axis of the holding element,
wherein the electrode carrier is arranged at an axial end of the holding rod which is remote from the linear guide,
wherein a resting part is arranged or formed at the holding element which resting part is designed for resting on a section of the ear,
wherein the holding rod comprises a first axis which runs in the region of the linear guide and parallel to the longitudinal axial of the holding rod,
wherein the holding rod runs from a first position, which adjoins to the linear guide, to a second position, which adjoins to the electrode carrier,
wherein the resting part defines a first plane with a resting area at the ear, on which area a second axis is arranged perpendicular,
wherein the first axis and the second axis span a middle plane, wherein
the holding rod lies at the first position in the or near the middle plane,
the holding rod departs from the middle plane from the run from the first position to the second position in a first rod section until a reversal point,
the holding rod moves to the middle plane from the run from the reversal point to the second position in a second rod section, so that it lies in the or near the middle plane after arriving of the second position, and
the electrode carrier, the electrodes, and at least the linear guide of the holding element are external to the ear.

2. The stimulation device according to claim 1, wherein the holding rod sinks between the first position and the second position, measured in the direction of the second axis, by a height displacement into the direction of the first plane.

3. The stimulation device according to claim 2, wherein the distance from the middle plane of the holding rod in the reversal point is between 30% and 60% of the height displacement.

4. The stimulation device according to claim 1, wherein the holding rod has a tangent at the first position which is directed into the direction of the first axis.

5. The stimulation device according to claim 1, wherein the holding rod has a tangent at the entry in the electrode carrier at the second position which encloses an angle to the first axis which is between 50° and 80°, seen in the direction of the second axis.

6. The stimulation device according to claim 1, wherein the holding rod has a swung run without any kink along its whole run from the first position to the second position.

7. The stimulation device according to claim 1, wherein the holding rod consists of an elastic material, especially of plastic material, at least in the region between the first position and the second position.

8. The stimulation device according to claim 1, wherein the electrical power supply of the at least one electrode takes place from the holding element via a cable, which runs separately between the holding element and the electrode carrier.

9. The stimulation device according to claim 1, wherein the holding rod consist of two parts, namely of a first part, which runs in the linear guide, and a second part, which runs between the first position and the second position.

10. The stimulation device according to claim 9, wherein the two parts of the holding rod are connected with another by means of a form fit connection.

11. The stimulation device according to claim 1, wherein the resting part of the holding element can rest at or in the Cavum conchae of the ear.

* * * * *